United States Patent
Cline et al.

(10) Patent No.: US 10,166,138 B2
(45) Date of Patent: Jan. 1, 2019

(54) OSTOMY APPLIANCE

(75) Inventors: John Cline, New Brunswick, NJ (US);
Bret Weig, Browns Mills, NJ (US);
Christopher Gregory, Newtown, PA (US); John Blum, Toms River, NJ (US)

(73) Assignee: Convatec Technologies, Inc., Las Vegas, NV (US)

( * ) Notice: Subject to any disclaimer, the term of this patent is extended or adjusted under 35 U.S.C. 154(b) by 580 days.

(21) Appl. No.: 12/664,169

(22) PCT Filed: Jun. 11, 2008

(86) PCT No.: PCT/US2008/066551
§ 371 (c)(1),
(2), (4) Date: Dec. 11, 2009

(87) PCT Pub. No.: WO2008/157172
PCT Pub. Date: Dec. 24, 2008

(65) Prior Publication Data
US 2010/0174253 A1    Jul. 8, 2010

Related U.S. Application Data

(60) Provisional application No. 60/943,322, filed on Jun. 12, 2007.

(51) Int. Cl.
*A61F 5/44* (2006.01)
*A61F 5/445* (2006.01)

(52) U.S. Cl.
CPC ...... *A61F 5/445* (2013.01); *A61F 2005/4455* (2013.01)

(58) Field of Classification Search
CPC ..... A61F 5/445; A61F 2205/4455; A61F 5/44
USPC .................................. 604/328, 327
See application file for complete search history.

(56) References Cited

U.S. PATENT DOCUMENTS

| | | | | |
|---|---|---|---|---|
| 2,243,529 A | * | 5/1941 | Jerg et al. | 600/32 |
| 2,544,201 A | * | 3/1951 | Wade | 604/328 |
| 3,216,420 A | * | 11/1965 | Smith et al. | 604/328 |
| 3,253,594 A | * | 5/1966 | Matthews et al. | 604/103.03 |

(Continued)

FOREIGN PATENT DOCUMENTS

WO    WO-9632904 A1    10/1996

OTHER PUBLICATIONS

European Patent Application No. 08780793.9 Supplementary European Search Report dated Feb. 22, 2017.

(Continued)

*Primary Examiner* — Philip R Wiest
*Assistant Examiner* — Guy Townsend
(74) *Attorney, Agent, or Firm* — Wilson Sonsini Goodrich & Rosati

(57) ABSTRACT

A stoma adapter is described that is especially suited to a recessed stoma or a flush stoma. The stoma adapter effectively extends the discharge passage from the stoma, protects peristomal skin, and forms a bridge at the interface between the stoma and an ostomy appliance. The stoma adapter contains a substantially unobstructed discharge passage, at least for effluent flowing in a discharge direction. The stoma adapter includes a seal for sealing against the bowel wall. The stoma adapter has collapsing, expanding, flexible and reinforced designs.

14 Claims, 13 Drawing Sheets

(56) References Cited

U.S. PATENT DOCUMENTS

| | | | | |
|---|---|---|---|---|
| 3,272,204 | A * | 9/1966 | Artandi | A61F 2/04 |
| | | | | 139/387 R |
| 3,374,856 | A * | 3/1968 | Wirt | F02K 1/827 |
| | | | | 138/121 |
| 3,447,533 | A * | 6/1969 | Spicer | 600/32 |
| 3,948,256 | A * | 4/1976 | Schneider | 604/344 |
| 4,086,665 | A * | 5/1978 | Poirier | 623/1.44 |
| 4,137,918 | A * | 2/1979 | Bogert | 604/328 |
| 4,182,339 | A * | 1/1980 | Hardy, Jr. | 606/154 |
| 4,209,010 | A * | 6/1980 | Ward et al. | 600/30 |
| 4,265,244 | A * | 5/1981 | Hill | 604/175 |
| 4,327,736 | A * | 5/1982 | Inoue | A61M 25/1027 |
| | | | | 604/101.05 |
| 4,555,242 | A * | 11/1985 | Saudagar | A61F 5/445 |
| | | | | 604/103.08 |
| 4,622,890 | A * | 11/1986 | Swanson | 99/450.2 |
| 4,650,463 | A * | 3/1987 | LeVeen et al. | 604/43 |
| 4,681,574 | A | 7/1987 | Eastman | |
| 4,721,508 | A * | 1/1988 | Burton | 604/338 |
| 4,728,328 | A * | 3/1988 | Hughes | A61B 17/11 |
| | | | | 623/1.32 |
| 5,188,623 | A * | 2/1993 | Kok et al. | 604/328 |
| 5,829,483 | A * | 11/1998 | Tukahara | F16L 9/18 |
| | | | | 138/109 |
| 5,833,915 | A * | 11/1998 | Shah | 264/491 |
| 5,871,536 | A * | 2/1999 | Lazarus | 623/1.13 |
| 5,891,113 | A * | 4/1999 | Quinn | A61J 15/0015 |
| | | | | 604/175 |
| 5,951,514 | A * | 9/1999 | Sahota | A61F 2/958 |
| | | | | 604/101.05 |
| 6,033,390 | A | 3/2000 | Von Dyck | |
| 6,485,476 | B1 * | 11/2002 | von Dyck | A61F 5/441 |
| | | | | 600/29 |
| 6,488,705 | B2 * | 12/2002 | Schmitt et al. | 623/1.18 |
| 6,491,067 | B1 * | 12/2002 | Davenport et al. | 138/110 |
| 6,805,662 | B2 * | 10/2004 | Shah et al. | 600/29 |
| 6,904,909 | B2 * | 6/2005 | Andreas | A61B 17/12104 |
| | | | | 128/200.24 |
| 7,001,367 | B2 * | 2/2006 | Arkinstall | 604/337 |
| 7,192,420 | B2 | 3/2007 | Whiteford | |
| 7,238,154 | B2 * | 7/2007 | Ewers | A61B 1/32 |
| | | | | 600/208 |
| 7,377,898 | B2 * | 5/2008 | Ewers et al. | 600/208 |
| 7,559,893 | B2 * | 7/2009 | Bonadio | A61B 17/0293 |
| | | | | 600/208 |
| 8,105,299 | B2 * | 1/2012 | Shah | A61F 5/445 |
| | | | | 604/327 |
| 8,167,859 | B2 * | 5/2012 | Shah et al. | 604/339 |
| 8,529,429 | B2 * | 9/2013 | Gobel | A61M 25/1002 |
| | | | | 600/32 |
| 8,568,477 | B2 * | 10/2013 | Lashinski et al. | 623/2.38 |
| 2005/0187578 | A1 * | 8/2005 | Rosenberg | A61M 25/04 |
| | | | | 606/232 |
| 2008/0188802 | A1 * | 8/2008 | Shah | 604/96.01 |
| 2008/0262449 | A1 * | 10/2008 | Shah | A61F 5/445 |
| | | | | 604/339 |
| 2010/0174253 | A1 * | 7/2010 | Cline | A61F 5/445 |
| | | | | 604/328 |

OTHER PUBLICATIONS

European Patent Application No. 08780793.9 Communication dated Mar. 14, 2017.

Mexican Patent Application No. MX/a/2009/013331 Office Action dated Apr. 28, 2017.

* cited by examiner

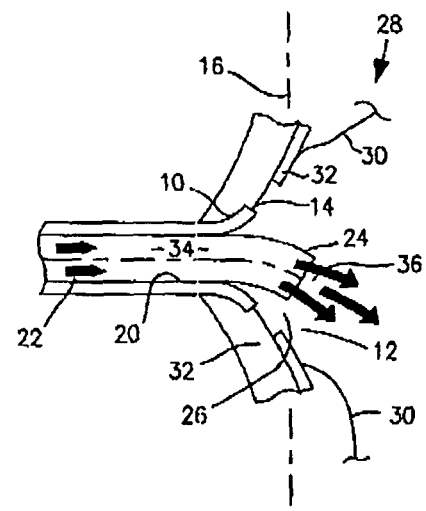
FIG. 1
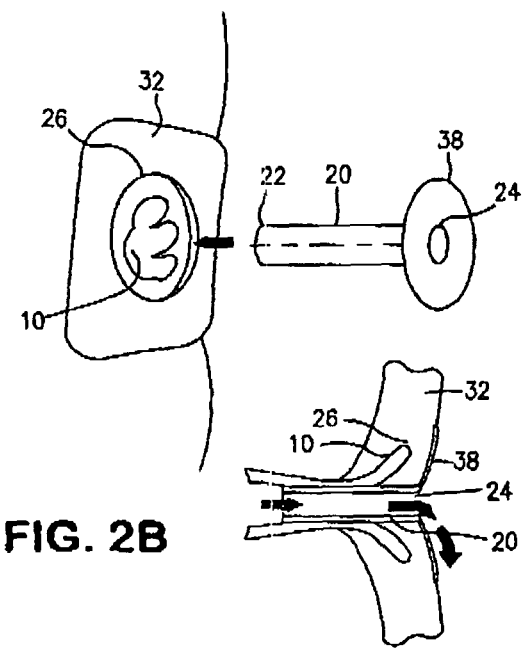
FIG. 2A
FIG. 2B

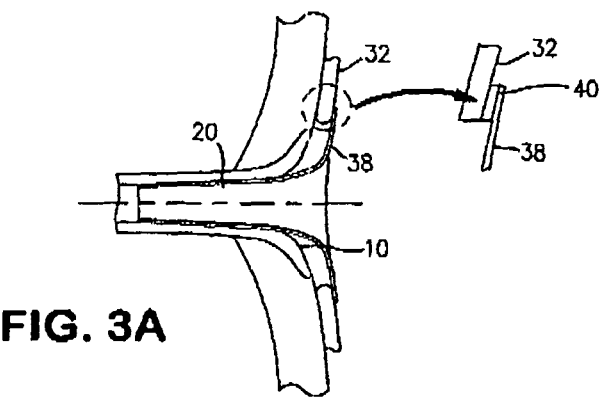
FIG. 3B
FIG. 3A
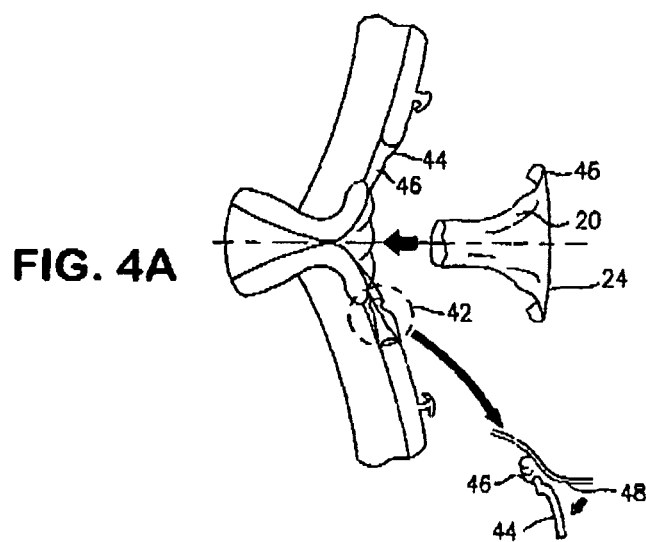
FIG. 4A
FIG. 4B

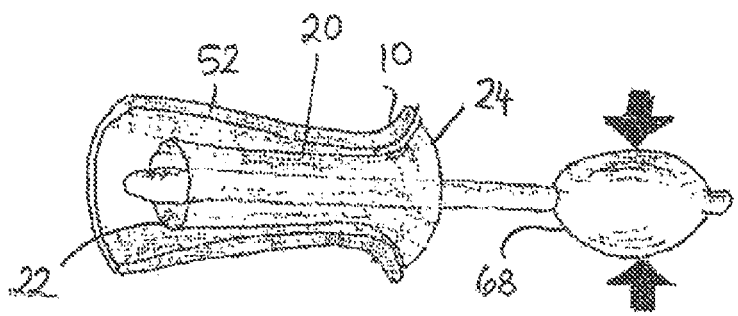
FIG. 12A
FIG. 12B
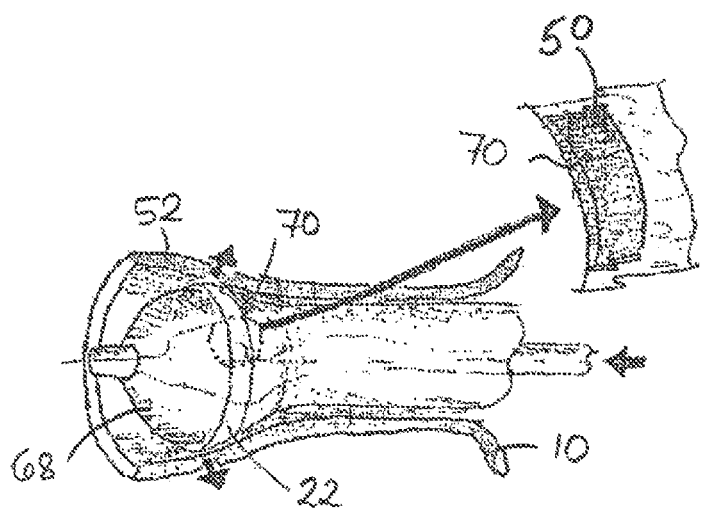
FIG. 12C
FIG. 12D

OSTOMY APPLIANCE

FIELD OF THE INVENTION

The present invention relates to an ostomy appliance. In particular, the invention relates to an ostomy appliance having a stoma adapter, and to a stoma adapter for an ostomy appliance.

BACKGROUND TO THE INVENTION

The creation of an ostomy (stoma) is the therapy for many sufferers of disease or injury of the gastrointenstinal or urinary tract. An ostomy is a rerouting of the tract through an opening or stoma in the abdominal wall to the outside of the body. The term "ostomy" typically includes colostomy, ileostomy and urostomy. Once this opening has been created, the patient must use an ostomy appliance attached to their body by some means to capture or manage the body waste. This is typically done with a disposable ostomy pouch that is attached to the patient's peristomal area by means of an adhesive. A typical ostomy appliance consists of an ostomy pouch and an adhesive body fitment. In some examples, the pouch and body fitment are separate components whereby a replacement pouch can be removably attached to the body fitment while the same body fitment remains attached to the body at the stoma site. In other examples, the pouch and the body fitment are permanently attached together, and are applied to and removed from the stoma site as an integral unit.

Ideally, the stoma should protrude from the abdominal surface of the ostomate by a distance ranging from 0.5 cm to 2.5 cm. This protrusion forms a spout, from which effluent can discharge directly into the pouch. However, in many cases, the stoma protrudes by a lesser amount or not at all. For example, a "flush stoma" is a condition when the stoma reaches only as far as the surface of the abdomen; a "recessed stoma" is a condition when the stoma does not even reach the surface of the abdomen, and the peristomal skin is drawn into a funnel shaped mouth between the stoma and the abdominal surface. There are many potential causes for these conditions. These can include formation of the stoma with little or no protrusion by the surgeon; and post-operative weight gain by the ostomate. Post-operative weight gain causes the ostomate's abdominal region to expand in girth while the length of the intestine attached to the abdomen remains fixed, thereby resulting in the stoma being pulled toward and ultimately below the surface of the abdomen.

Flush and recessed stomas can be difficult to manage, because some effluent discharged from the stoma can tend to pool around the stoma, instead of the effluent discharging completely into the pouch. Stool retained in this manner can attack the interface between the adhesive body fitment and the ostomate's peristomal skin. Such attack reduces the adhesion of the body fitment to the skin, thereby reducing the effectiveness and the usable life of the appliance. The stool can also cause irritation and degradation of the peristomal skin itself. Stool exiting the stoma may contain digestive juices from the body, and such juices can attack the peristomal skin resulting in excoriation.

One current technique for dealing with a flush stoma and/or a recessed stoma is to use a body fitment with a convex pressure plate to apply increased local pressure to the skin immediately adjacent to the stoma. The increased pressure protrudes the stoma slightly, but a strong adhesion of the body fitment to the peristomal skin may be required to bear the reaction force.

U.S. Pat. No. 6,033,390 describes a continent ostomy port that includes a tube inserted into the stoma, and a closure for selectively closing a discharge channel within the tube. This device is for general stomas, and does not address the problem of recessed or flush stomas. A primary function of the device is to act as a controllable closure, for blocking discharge of effluent when desired by a user. However, the existence of the closure means that the tube inserted into the stoma has to form a strong seal against the stoma tissue, in order to withstand the pressure of effluent backing up inside the intestine, and to prevent such effluent from leaking between the stoma tissue and the inserted tube.

It may be desirable to provide an alternative technique for a flush stoma and/or a recessed stoma.

SUMMARY OF THE INVENTION

The present invention provides a stoma adapter for at least partial insertion into a stoma and/or into a peristomal mouth surrounding a recessed stoma.

The stoma adapter may be configured as one or more of the following:
(a) A stoma extension, for extending the discharge passage in a stoma to a location external of the stoma, in order to deliver effluent to a point relative to the ostomy appliance from which the effluent can more directly discharge into the interior of the appliance than were the adapter not present.
(b) A stomal effluent diverter, for diverting or directing effluent exiting the stoma away from contact with peristomal skin and/or away from contact with an edge of the skin adhesive of an adhesive body fitment.
(c) A liner for protecting peristomal skin, and/or an edge of the skin adhesive of an adhesive body fitment, from contact with stoma effluent. The liner may extend into the interior of the stoma as a stoma liner.

The stoma adapter is especially suitable for a flush stoma or a recessed stoma, but is not limited thereto.

In one form, the stoma adapter extends closer to the stoma than does the skin adhesive of the adhesive body fitment.

In one form, the stoma adapter may be separate from the body fitment of an ostomy appliance. In another form, the stoma adapter is releasably attached to the body fitment, for example, by an adhesive coupling or a mechanical interference coupling. In yet another form, the stoma adapter is permanently secured to the body fitment as an integral part.

In one form, the stoma adapter is elongate and/or tubular. The stoma adapter may include a discharge passage that is longer than at least the minimum transverse dimension (and optionally longer than the maximum transverse dimension).

In one form, the stoma adapter (at least once fitted to a stoma) defines a substantially unobstructed discharge channel for effluent discharging from the stoma. The stoma adapter may be referred to as a free-flow stoma adapter (and/or a free-flow diverter). The stoma adapter may be permanently open. In another form, the stoma adapter includes a valve. The valve is openable under pressure of effluent when the bowel forces the expulsion of effluent. The valve does not block stomal discharge, but merely provides a partial closure to avoid the stoma being permanently open. The valve could be a one-way valve, to avoid entry of external matter into the stoma.

Making the discharge channel substantially unobstructed for stomal discharge reduces the stress to which the seal between the stoma adapter and the stoma tissue will be subject in use, compared to the seal stress of a continent ostomy port with a permanent tube having a closable discharge channel. With less seal stress to withstand, the stoma adapter can be configured to engage the stoma tissue much more lightly and gently than a continent ostomy port.

In effect the functions of the stoma adapter of the present invention and a continent ostomy port are quite contrary. The continent stoma port seeks to provide a firm engagement against the stoma tissue to provide a reliable closure that prevents stoma discharge; whereas the present invention seeks to provide a minimum engagement against the stoma, in order to provide a substantially unobstructed discharge channel that delivers stomal discharge away from the peristomal skin.

It should be noted for the purpose of clarity that, in this document, "proximal" refers to an object, feature, or general direction toward the inside of the body. "Distal" refers to an object, feature, or general direction toward the outside of the body.

Accordingly, the present ostomy device has a stoma adapter that directs stomal effluent from the bowel into a collection pouch. The device covers the peristomal skin and the interface between the skin and the ostomy appliance. The device can be partly or fully inserted into the stoma. It also may be an open-ended tube. The tube can be rigid. Another possible form is that it is partially deformed by forces applied by the bowel, but remains open throughout its length.

The tube thickness can be in the range of 0.0001 inch to 0.20 inch. The tube can be reinforced so as to provide stiffness in the axial direction while permitting flexure in the radial direction. An example of reinforcement is an array of longitudinal elements located around the circumference of the tube and which are oriented generally parallel to the axis of the tube, wherein the largest cross-section dimension of each element is less than 10% of the largest cross-section width of the tube.

Option for reinforcement elements include: a hollow cross-section, inflatability, flexible material composition, formation of elements by selectively attaching multiple layers of the tube wall together to form a hollow cavity, a helical compression spring attached to or imbedded in the tube. The compression spring may, for example, be composed of resilient material or of a hollow tube having no intrusive resilience but becomes resilient when inflated.

Reinforcement can also be accomplished with a pattern of selective coating on the tube to locally modify its properties and wherein the result of this pattern is an increase in axial stiffness of the tube.

The tube may have other properties such as being at least partially collapsed in cross-section to reduce its cross-sectional width wherein the tube can subsequently expand to its final cross-sectional shape. Others include wherein the tube is bistable and retains its folded shape until it is deliberately expanded or wherein the tube is held in its folded shape by a retaining member.

It is possible to have a tube that is sufficiently flexible that its bore can be closed by forces applied by the bowel.

Example of a retaining member shapes includes generally cylindrical, or conical. The retaining member may be of the type that may be broken or dissolved to allow the tube to expand. The retaining member can be removed off of the proximal or distal end of the tube.

Dissolution of the retaining member can be accomplished by forming the device of one or more water soluble polymers such as polysaccharides, cellulosics such as hydroxypropylmethyl cellulose, hydroxyethyl cellulose, hydroxypropyl cellulose, carboxymethyl cellulose, chitosan and its derivatives, gelatin, alginates, sodium alginate, xanthan gum, tragacantha, guar gum, acacia gum, arabic gum, polyacrylic acid and its copolymers, polypeptides, sulfonated polymers, polyacrylamide and its copolymers, polyvinyl pyrrolidone, polyvinyl ether, polyvinyl alcohol, polyethylene, glycol, methylmethacrylate copolymers, carboxyvinyl polymers and copolymers.

The device may be formed, for example, from one or more of the following materials: cellulosic polymers, alginates, chitosan and its derivatives, polyesters, polyacrylonitriles, polyolefins, diene elastomers, polyamides, polyurethanes, polyethers, polyvinyl alcohol, polyether block amides, polyimides, silicones, polyacrylates, polymethacrylates, ionomers, polyvinylacetate and its copolymers, polyvinylchloride, polyvinylidene chloride, or fluorinated polymers.

Ways of forming the stoma adapter include injection molding, thermoforming, blow molding, casting, extrusion or fabrication form sheet stock.

The proximal portion of the device seals against the inner bowel wall for at least part of its length. The distal end of the device may be attached to and seal against the wearer's peristomal skin. Also, the distal end of the device may be attached to and seal against the proximal side of the ostomy wafer and the distal surface of the ostomy wafer.

The stoma adapter may be partly retained in place by an attachment at its distal and/or proximal end. Different ways of attaching or retaining the distal end include utilizing an adhesive bond, a solvent bond, a heat weld, an ultrasonic weld, a radio frequency weld, a laser weld, a mechanical interference, or a mechanical snap ft. Retention of the proximal end can be achieved with material that includes an adhesive gel or coating that adheres the seal to the inner bowel wall. The material can be coated onto the seal prior to insertion or it can be dispensed from the seal after the device has been introduced into the bowel.

The seal is formed from a resilient polymer, elastomer or foam that is at least partly plastically deformable. The seal may have an annular shape. The seal can be created at the proximal end of the device.

The seal may be an expanding inflatable volume formed from a flexible material, such as a film. The seal inflation material may be a gas, liquid or gel.

The seal material may include a resilient foam member and may cause the seal to inflate.

In certain forms, the device can be inserted directly into the stoma. Another possible way to insert a flexible stoma adapter is to partially invert it one or more times along its length so that the device can be introduced into the stoma by temporarily closing the proximal end and pressurizing the distal end.

Additional features and/or aspects of the invention are defined in the claims and/or apparent from the following description. Although certain features have been highlighted above and in the appended claims, claim protection may be sought for any inventive feature and/or idea described herein and/or illustrated in the drawings, whether or not emphasis has been placed thereon.

BRIEF DESCRIPTION OF THE DRAWINGS

FIG. 1 is a schematic sectional view through a first embodiment of stoma adapter.

FIG. 2A is a schematic perspective view of a second embodiment of stoma adapter.

FIG. 2B is a schematic sectional view showing the second embodiment in use.

FIG. 3A is a schematic sectional view through a third embodiment of stoma adapter.

FIG. 3B is a magnified view showing a detail of FIG. 3A.

FIG. 4A is a schematic sectional view through a fourth embodiment of stoma adapter.

FIG. 4B is a magnified view showing a detail of FIG. 4A.

FIG. 12A is a schematic sectional view showing an eleventh embodiment of stoma adapter in use.

FIG. 12B is a schematic sectional view showing an eleventh embodiment of stoma adapter in use.

FIG. 12C is a schematic sectional view showing an eleventh embodiment of stoma adapter in use.

FIG. 12D is a magnified view of a detail of FIG. 12C.

DETAILED DESCRIPTION OF PREFERRED EMBODIMENTS

Figure 4C:
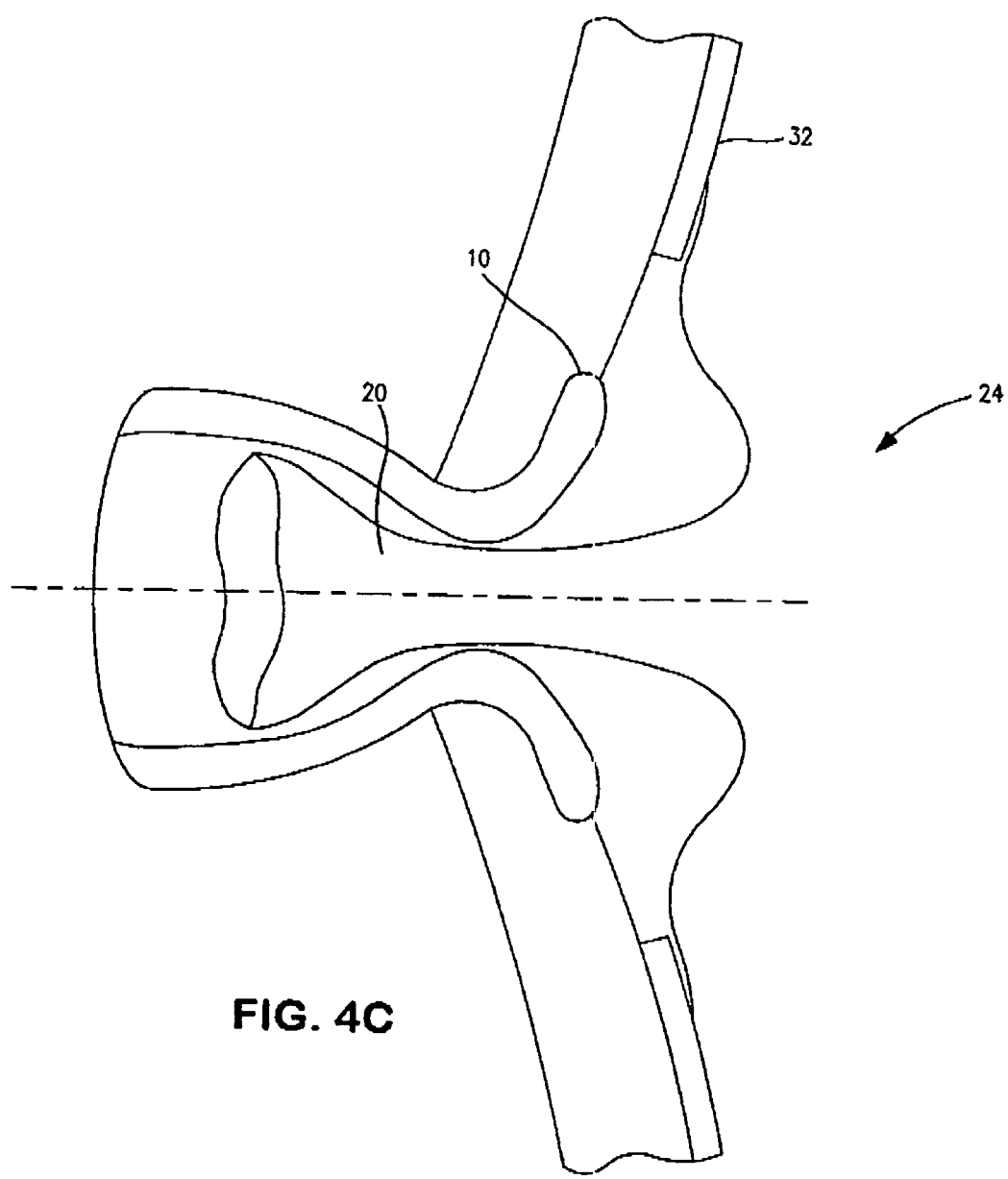
FIG. 4C is a sectional view of the fourth embodiment showing the distal end extending beyond the attachment plane of the body fitment.

Referring to the drawings, the same reference numerals are used to depict the same or similar features. The features of the following embodiments may be combined as desired; the separate description of features as different embodiments is mainly to ease clarity, and does not in any way mean that certain features should not or cannot be used together.

Referring to FIG. 1, a recessed stoma 10 is illustrated, in which the stoma 10 is joined to the peristomal skin 12 at a point 14 that is slightly below the abdominal skin level 16. A most basic form of stoma adapter 20 comprises, or is in the form of, a tube having a proximal end 22 inserted into the stoma 10 and into the funnel shaped mouth defined by the peristomal skin around the recessed stoma 10, at least to the level of the stoma 10. The stoma adapter 20 has a distal end 24 that projects beyond the abdominal skin level 16. The distal end 24 may optionally be angled to direct stomal discharge downwardly, if desired. The distal end 24 projects at least partly into the entrance aperture 26 of an ostomy appliance 28 comprising a collection pouch 30. The ostomy appliance 28 is secured to the peristomal skin 12 by means of an adhesive body fitment 32 comprising or consisting of an adhesive wafer. The ostomy appliance 28 may be a one-piece appliance in which the body fitment 32 is permanently attached to the pouch 30, or it may be a two-piece appliance in which the pouch 30 may be releasably attached to the body fitment 32 by means of a releasable coupling (not shown) such as an adhesive coupling or a mechanical interference coupling.

The stoma adapter 20 defines a free-flow, substantially unobstructed, passage 34, to deliver stomal discharge from the proximal end 22 inserted at the stoma 10, to the distal end 24 projecting into the entrance aperture 26 of the ostomy appliance 28. The stoma adapter 20 thus closely approximates the function of a stoma with an "ideal" protrusion from the peristomal skin. The stoma adapter 22 functions as a stoma extender and/or a stoma effluent diverter and/or a stoma liner. The stoma adapter 20 diverts stomal discharge away from the peristomal skin 12, directly into the interior of the ostomy appliance 28. By keeping the stomal discharge clear of the peristomal skin 12: (i) the risk of the effluent attacking the adhesion between the body fitment 32 and the peristomal skin 12 is reduced, thereby leading to better product life; and/or (ii) the risk of irritation or excoriation of the peristomal skin 12 is very much reduced.

The stoma adapter 20 may be relatively short, such that the proximal end 22 does not extend very far into the stoma 10 (or even is inserted merely to the point 14 at which the stoma 10 meets the peristomal skin 12). Alternatively, the stoma adapter 20 may be relatively long such that it extends more substantially into the stoma 10. The stoma adapter 20 preferably defines a discharge passage 34 that has a longitudinal (axial) dimension that is greater than a minimum transverse dimension (or more preferably greater than a maximum transverse dimension).

The stoma adapter 20 may be permanently open, to define the free-flow discharge passage 34. Alternatively, the stoma adapter 20 may comprise a valve (depicted generally by the numeral 36). The valve 36 may be disposed at any desired location, for example, at the proximal end 22 or the distal end 24, or intermediate the two. The valve 36 may be configured as a closed end of the tube. The valve 36 is configured not to obstruct the discharge of effluent, and is configured to open under the pressure of effluent when the bowel forces the expulsion of effluent. The valve 36 may be a one-way valve.

In the embodiment of FIG. 1, the stoma adapter 20 is generally independent of the ostomy appliance 28 and the body fitment 32.

FIGS. 2a and 2B illustrate a second embodiment in which the distal end 24 of the stoma adapter 20 comprises a shoulder or flange 38. The flange 38 acts as a stop to limit the degree of insertion of the stoma adapter 20 into the stoma 10. In the present embodiment, the flange 38 additionally is dimensioned to engage the body fitment 32. For example, the flange 38 is slightly larger in diameter than the entrance aperture 26 in the adhesive body fitment 32. The flange 38 is configured to engage the rear surface (in FIG. 2B) or alternatively the front surface (not shown) of the body fitment 38. For a one-piece appliance, the stoma adapter 20 can be inserted at the stoma 10 before the body fitment 32 of the ostomy appliance 28 is attached to the peristomal skin 12, such that the periphery of the flange 38 is trapped between the skin 12 and the body fitment 32 to hold the stoma adapter 20 positively in position.

FIGS. 3A and 3B shows a modified third embodiment similar to the second embodiment, except for the following refinements:

The flange 38 is implemented with a rounded funnel shape that joins the tubular portion of the stoma adapter 20 to define a smoothly rounded tapering profile.

The flange 38 is releasably or permanently attached to the body fitment 32, at a point of attachment indicated generally by numeral 40. The point of attachment 40 may on the distal (front) surface of the adhesive. Such a configuration provides direct transport of effluent from the bowel into the pouch, bypassing peristomal skin 12 between the stoma 10 and the inner edge of the adhesive wafer of the body fitment 32. It also bypasses the interface between the peristomal skin 12 and the body fitment 32. Attachment between the stoma adapter 20 and the body fitment 32 may be accomplished by a variety of means, including adhesive bonding, solvent bonding, and welding (e.g., heat welding, ultrasonic welding, laser welding, or radio frequency welding). The attachment point 40 may also be adhesive attachment using the adhesion of the skin adhesive in the body fitment 32. In the case of any of the adhesive types of attachment, the attachment may be permanent or releasable (e.g., peelable) as desired.

FIGS. 4A and 4B show a modified fourth embodiment similar to the second and third embodiments, except the fourth embodiment uses a mechanical fastener 42 to join the distal end 24 of the stoma adapter 20 to the body fitment 32. The mechanical fastener 42 comprises mating rings 44 and 46 on the body fitment 32 and the stoma adapter 20. For example, the ring 46 of the stoma adapter 20 may form a snap fit behind the ring 44 on the body fitment 32, to be trapped between the body fitment 32 and the peristomal skin 12. The mechanical fastener 42 may be releasable while the body fitment 32 remains in place on the peristomal skin 12, or the fastener 42 may be configured as non-releasable (e.g., at least until the body fitment 32 is removed). The mechanical fastener 42 may be augmented by an adhesive attachment (indicated between the parts at 48) and/or seal that would also provide an adhesive connection between the stoma adapter 20 and the body fitment 32.

Also, in the fourth embodiment, the stoma adapter 20 generally has a more conic shape, at least towards the distal end 24, so that the flange is less pronounced.

As seen in FIGS. 4B and 4C, the distal end 24 of the stoma adapter 20 may extend out past the stoma 10 and then return to attach to the body fitment 32. Such a shape would allow the stoma adapter 20 to move axially with the stoma 10 without placing unwanted stress on the attachment to the body fitment 32.

Formation of the stoma adapter 20 can be accomplished by a variety of methods. These include, but are not limited to, injection molding, blow molding and longitudinal seal bonding of flat sheet material to form a tube. The tube material may or may not, as desired, have gas barrier properties to contain or manage odor. The stoma adapter 20 material may or may not, as desired, have properties that reduce the friction of effluent flow along its length, in order to promote easier discharge of effluent. The stoma adapter 20 may or may not, as desired, have properties that improve ease of introduction into the bowel. These properties may be imparted by the material itself, by impregnating the material with specific additives intended to impart those properties to the material, or by application of one or more coatings to the appropriate surface(s) of the stoma adapter 20.

The preferred cross-sectional shape of the stoma adapter 20 in the embodiments is circular, but in some cases, it may be desirable for the stoma adapter 20 to have a conic, but non-circular shape. It may also be desirable for the stoma adapter 20 to have a cross-sectional shape that closely approximates the shape of the inner surface of the bowel to ensure that it conforms to the bowel along the full length of the stoma adapter 20. This may be accomplished by creating a custom shape for each stoma adapter 20 to match the wearer. It may also be accomplished by imparting elastic properties to the stoma adapter 20 that cause it to deform to match the shape of the bowel after introduction. These changes may be purely elastic, in which the stoma adapter 20 regains its original shape after removal. Or, the changes may be entirely plastic, in which the adapter 20 retains the shape of the inner surface of the bowel. Or, the changes may be a combination of elastic-plastic behavior, in which the stoma adapter 20 partially retains the shape of the bowel after removal. Materials for such a stoma adapter 20 include, but are not limited to, biocompatible materials of natural or synthetic origin, such as olefin plastics, polycarbonates, styrenes, flouropolymers, thermoplastic elastomers, polyurethanes, polyesters, cellulose polymers, alginates, chitosan and its derivatives, polyacrylonitriles, diene elastomers, polyamides, polyethers, polyvinyl alcohol, polyether block amides, polyimides, silicones, polyacrylates, polymethacrylates, ionomers, polyvinylacetate and its copolymers, polyvinylchloride, polyvinylidene chloride, and fluorinated polymers. Composite construction including one or more of the above and/or metallic elements such as springs, may also be desirable. Shape memory metals or polymers may be suitable for the shape recoverable embodiments illustrated later. Methods of formation of such a stoma adapter 20 may include, but are not limited to, any of injection molding, thermoforming, extrusion, casting, blow molding, sterolithography, or fused deposition, or selective laser sintering.

The properties of the stoma adapter 20 may vary depending on the design and the intended application. For example, a rigid stoma adapter 20 (as in the first to third embodiments) may be useful for holding the bowel open and to maintain a constantly open flow path for efficiently directing effluent from the bowel.

Figure 5:
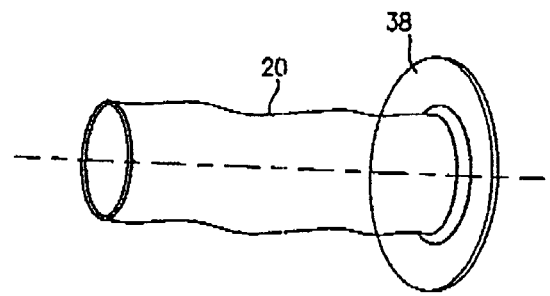
FIG. 5 is a schematic perspective view of a fifth embodiment of stoma adapter

Alternatively, the stoma adapter 20 may be formed of thin, flexible material such a plastic film (as in the fourth embodiment, and a fifth embodiment illustrated in FIG. 5). The flexible material may or may not have elastic properties, as desired. Use of a flexible material may be suitable for where compatibility with natural movements of the bowel is desired. The bowel typically changes its cross-sectional shape as a result of a variety of conditions. These include normal peristaltic motion, flexure of the abdominal wall, vigorous physical activity, and the passage of effluent through the bowel. A stoma adapter 20 made from thin, flexible material may be used where it is desired to present little or no hindrance to natural motion of the bowel.

A further aspect of the stoma adapter 20 is the creation of a seal between the bowel wall 52 and the stoma adapter 20. The following embodiments illustrate certain seal principles. Although these embodiments illustrate seal features separately, the sealing arrangements may be combined, and any of the seal arrangements may be used with any of the preceding embodiments.

Figure 6:
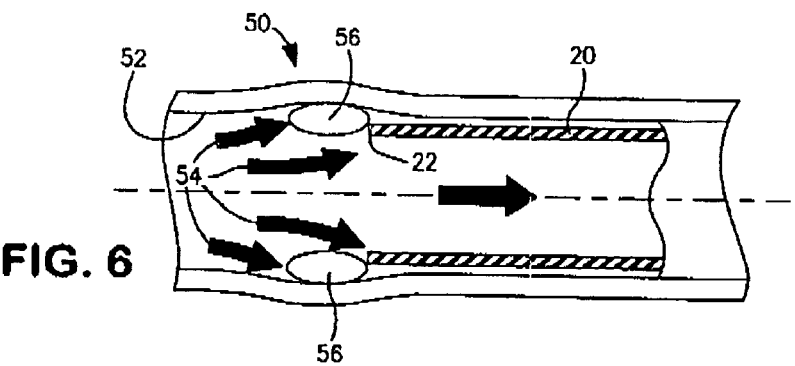
FIG. 6 is a schematic sectional view through a sixth embodiment of the stoma adapter.
Figure 7:
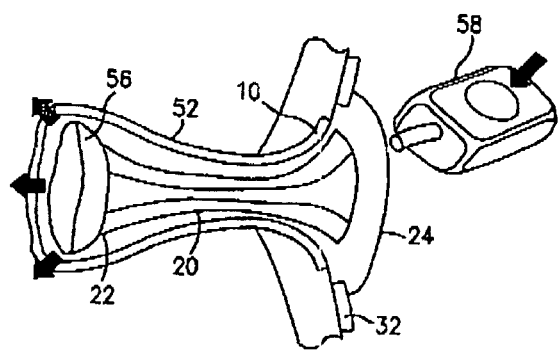
FIG. 7 is a schematic sectional view showing deployment of the sixth embodiment.

Referring to FIGS. 6 and 7, in a further embodiment, the proximal end 22 of the stoma adapter 20 incorporates a seal 50 between the inner surface of the bowel wall 52 and the outer surface of the stoma adapter 20. Because the stoma adapter 20 is configured not to obstruct the free flow of effluent in the discharge direction, and is not intended to be closed or to block flow, the intent of the seal 50 is merely to divert the flow of effluent into the stoma adapter 20 (as indicated by arrows 54). The seal 50 does not have to withstand the pressure of effluent backing up inside the bowel. In the preferred embodiments, the seal 50 performs the function of flow diversion with a minimum level of pressure exerted on the bowel tissue. It is desirable to create a seal that conforms to the local shape and topography of the inner surface of the bowel wall 52.

In the embodiment of FIGS. 6 and 7, the seal 50 is provided by a bolster 56. The bolster 56 is optionally inflatable to expand into seal contact with the inner surface of the bowel wall 52. Inflation fluid may be supplied from an external source 58 through an inflation capillary channel (not shown). The inflation pressure would be a minimum required to create an effective seal, to ensure that blood flow through the bowel and to local seal contact area would not be compromised.

Figure 8A:
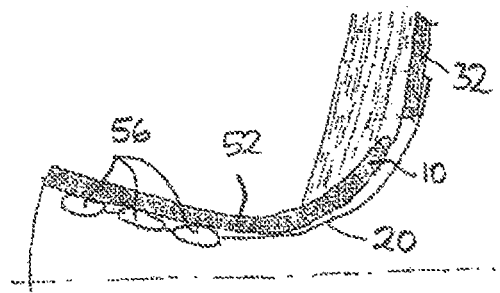
FIG. 8A is a schematic sectional view through a seventh embodiment of stoma adapter.
Figure 8B:
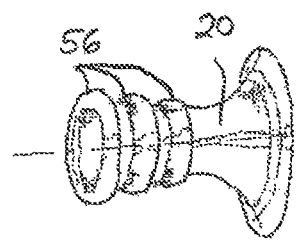
FIG. 8B is a schematic perspective view of the seventh embodiment.

Referring to FIGS. 8A and 8B, in a further embodiment, the seal 50 comprises two (or more) distinct inflatable sealing elements or bolsters 56. The bolsters 56 are radially and/or axially displaced from each other. The bolsters 56 may be inflated to the same inflation pressure, or different inflation pressures. The bolsters 56 may be inflated from a common inflation port (optionally, with some inflation pressure regulator if the bolsters 56 are to be inflated to different inflation pressures), or from independent inflation ports to allow complete control over each respective inflation pressure. Two or more bolsters 56 may be desirable in certain applications.

With the embodiments of FIGS. 6-8, the inflation fluid may be a gas (such as air) or a liquid (such as saline), or a gel, or any suitable fluid that can be transferred from one volume to a second volume to expand the second volume. The inflation fluid may retain its properties, or it may set into a rigid or semi-rigid state after filling the inflatable bolster 56.

Figure 9A:
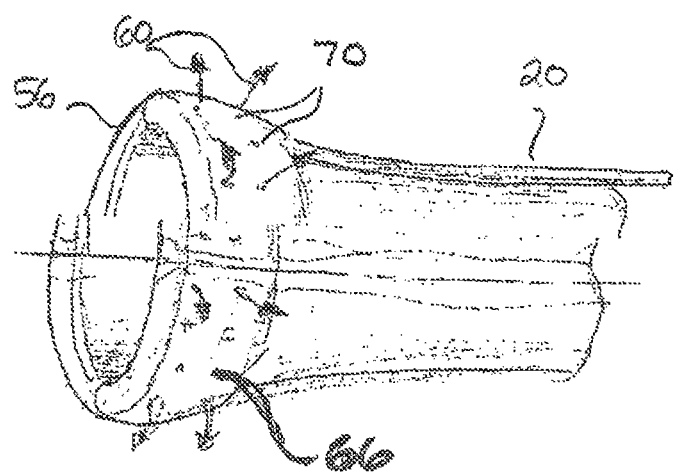
FIG. 9A is a schematic perspective view showing the proximal end of an eighth embodiment of stoma adapter.
Figure 9B:
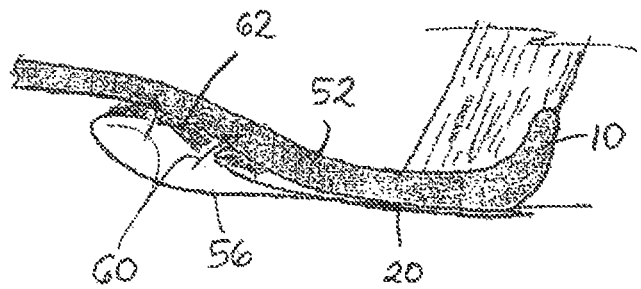
FIG. 9B is a schematic sectional view through the proximal end of the eighth embodiment.

Referring to FIGS. 9A and 9B, the inflation fluid could be or comprise a sealant material. Furthermore, the bolster 56 may be configured to permit the sealant to pass through the wall(s) of the bolster 56 to form a seal between the bolster 56 and the bowel wall 52. For example, the bolster 56 may have small (e.g., microscopic) holes 66 in specific areas that contact the bowel wall 52, in order to preferentially pass the sealant 62 (as indicated by arrows 60) to the corresponding region of the bowel wall 52, to fill any gaps (indicated by the sealant filling 62 in FIG. 9B).

Figure 10A:
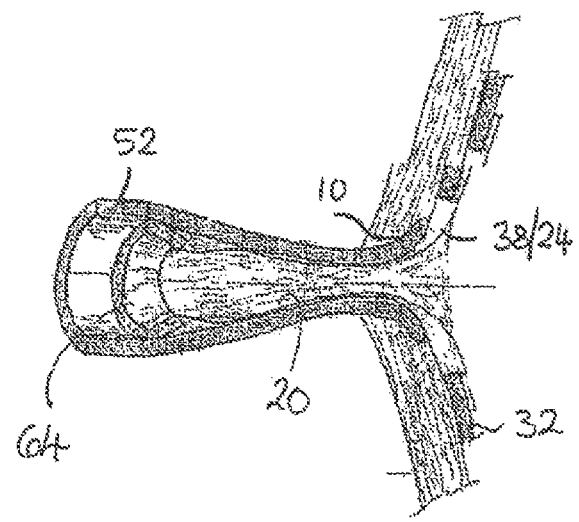
FIG. 10A is a schematic sectional view through a ninth embodiment of stoma adapter in use.
Figure 10B:
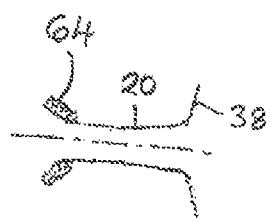
FIG. 10B is a schematic section through the ninth embodiment in isolation.

Referring to FIGS. 10A and 10B, instead of an inflatable bolster 56, the stoma adapter 20 comprises an annular foam ring 64 to contact the inner surface of the bowel wall 52 and create a seal. The foam ring 64 is optionally shaped to improve its sealing properties. The thickness of the foam, and/or the diameter of the foam, and/or the contact angle of the foam can also be adjusted to optimize the sealing characteristics. In the illustrated embodiment, the foam ring has a conical shape, presenting a funnel-like geometry to the flow of effluent. The inner and/or outer surface may be frusto-conical. Other shapes of foam ring 64 could be used as desired. For example, the foam ring could alternatively have a cylindrical annular shape, whose cross section is oriented generally perpendicular to the surface of the inner bowel wall 52.

The properties of the foam may also be adjusted to improve the properties of the seal. The foam may be open or closed cell construction, depending on the requirements of the application. Elastic properties of the foam could be adjusted to ensure the proper balance between sealing pressure and seal performance.

Figure 10C:
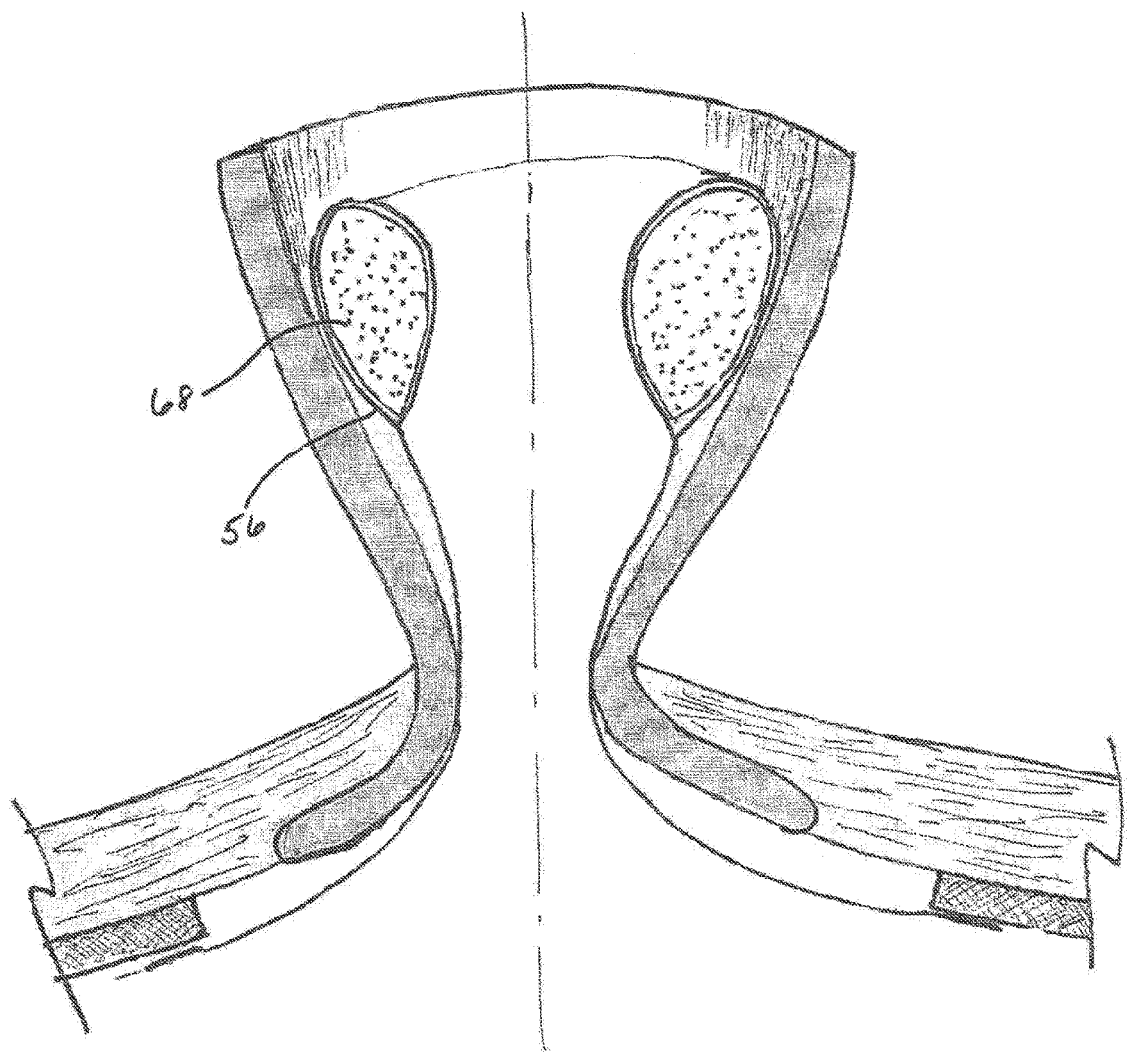
FIG. 10C is a sectional view of the ninth embodiment showing an expandable foam element within an inflatable bolster.

Referring to FIG. 10C, the bolster 56 may enclose a expanding foam element 68. The preferred embodiment of the foam element 68r is an annular ring, although other symmetrical or non-symmetrical shapes may be preferred for specific applications. The natural tendency of the foam element 68 to expand would inflate the bolster 56 and cause it to conform to the size and shape of the bowel wall 52. As the foam element 68 expands, air or any other suitable inflation fluid would be drawn into the bolster 56.

It is possible to control the response of the foam-filled bolster 56 by controlling the rate at which inflation fluid enters and exits the bolster 56. This response could include, but not be limited to, inflation with little or no flow restriction and deflation with a high flow restriction.

Figure 11:
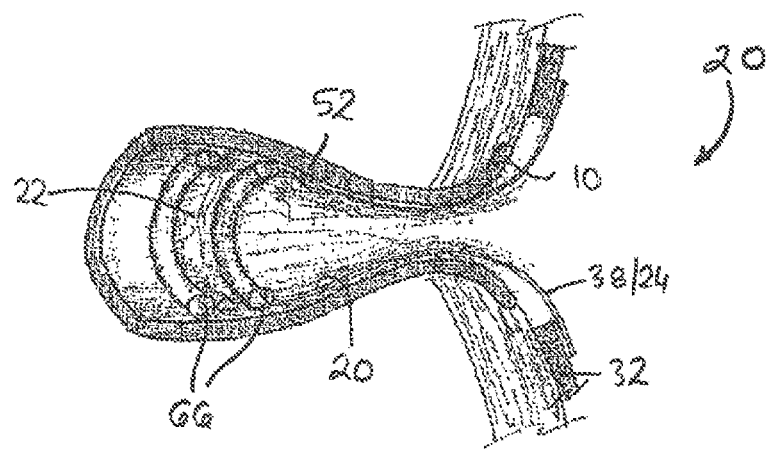
FIG. 11 is a schematic section through a tenth embodiment of stoma adapter.

Referring to FIG. 11, in another embodiment, one or more elastomeric rings 66 located at the proximal end 22 of the stoma adapter 20 serve to hold the proximal end 22 of the tube in sealing contact with the inner surface of the bowel wall 52. Two or more of these elastometric rings 66 could be axially displaced along the tube of the stoma adapter 20. The elastometric rings 66 may optionally be of different diameters, to improve the adapter's ability to effectively seal against a surface that is different in size from one ostomate to another, and which may change in size continually.

Referring to FIGS. 12A, 12B, 12c and 12D, in another embodiment, the proximal end 22 of the stoma adapter 20 is plastically deformable. In use, when inserting the stoma adapter 20 into the stoma 10, the proximal end 22 is stretched circumferentially until it achieves conformal contact with the inner surface of the bowel wall 52. Stretching of the proximal end 22 of the stoma adapter 20 could be achieved by means of an inflatable bolster 56 which would be removed after creation of the seal 50. The function of the seal 50 could be enabled or enhanced by the application of a sealant or an adhesive (region 70) to the contact area of the seal before introduction or during manufacture.

Another aspect of the stoma adapter 20 is retention in the stoma and/bowel. The following embodiments illustrate various retention principles. Although these embodiments illustrate retention features separately, the retention arrangements may be combined, and any of the retention arrangements may be used with any of the preceding embodiments.

In some applications, retention of the stoma adapter 20 in the bowel is significant for its function. In the case of a rigid or semi-rigid stoma adapter 20, then it is possible to ensure retention of the proximal end 22 in the bowel by anchoring the stoma adapter 20 externally to the bowel. For example, attaching the distal end 24 of the stoma adapter 20 to the distal surface of the body fitment 32, to the pouch 30, or directly to the ostomate's peristomal skin 12 could achieve that anchoring function (as illustrated in FIGS. 3*a*, 3B, 4A and 4B).

In the case of a stoma adapter 20 that is constructed wholly or partially of thin, flexible material, it may be desirable to prevent the stoma adapter 20 from collapsing along its axis due to peristaltic forces or the force of expelled effluent. One method of ensuring retention of a flexible tubular stoma adapter 20 is to reinforce it in the axial direction without adversely affecting its ability to conform to the inner surface of the bowel wall 52. The axial stiffness supports the proximal end 24 of the stoma adapter 20 in the same way that a rigid or semi-rigid stoma adapter.

Figure 13A:
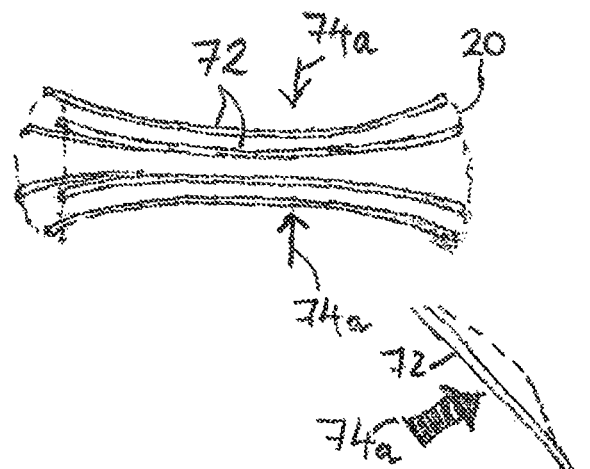
FIG. 13A is a schematic perspective view of a twelfth embodiment of stoma adapter.
Figure 13B:
FIG. 13B is a schematic diagram illustrating flexing of the twelfth embodiment in use.
Figure 13C:
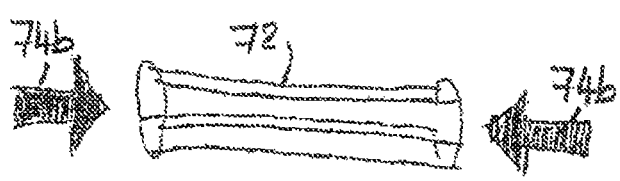
FIG. 13C is a schematic diagram illustrating flexing of the twelfth embodiment in use.

Referring to FIGS. 13A, 13B and 13C, one means of providing axial stiffness to incorporate a multiplicity of buttress or reinforcing elements 72 on the outer or inner surface of the stoma adapter 20. The reinforcing elements 72 are oriented generally parallel to the tubular axis of the stoma adapter 20. The size, number, and placement of the reinforcing elements 72 would determine the axial stiffness of the stoma adapter 20. However, because the individual reinforcing elements 72 are relatively compliant in the transverse direction, the tubular stoma adapter 20 would remain radially flexible (see arrows 74*a* indicating flexing in the radial direction when squeezed; and arrows 74*b* representing withstanding of an axial force).

Figure 14A:
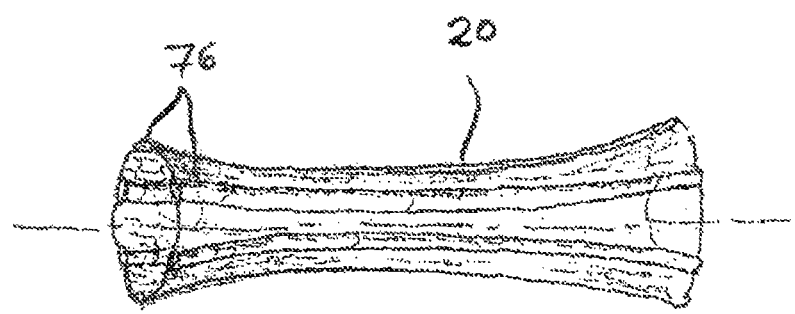
FIG. 14A is a schematic perspective view of a thirteenth embodiment of stoma adapter.
Figure 14B:
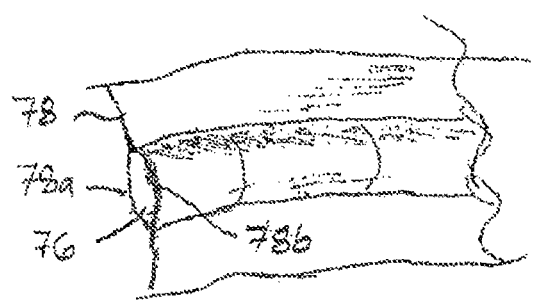
FIG. 14B is a magnified view of a detail of FIG. 14A.

Referring to FIGS. 14A and 14B, in another embodiment of this axial buttress or reinforcement approach, the surface of the stoma adapter 20 includes a multiplicity of tubes 76 (flexible capillaries) running length of the stoma adapter 20. These tubes 76 are smaller in cross section than the main discharge passage 34 of the stoma adapter 20, with cross section widths less than 25% of the cross section width of the discharge passage 34. These tubes 76 can be formed from very soft material. In one form, the tubes 76 are additional components assembled to the stoma adapter 20; in another form, the tubes 76 are integrally formed as part of the structure of the stoma adapter 20 itself. For example, the smaller tubes 76 are formed by selectively attaching together portions of adjacent layers 78*a*, 78*b* of the material forming the multi-layer wall 78 of the stoma adapter 20. In use, inflation of the tubes 76 imparts axial rigidity to them, and therefore to the stoma adapter 20. At the same time, the tubes 76 are compliant to local radial forces. The smaller tubes 76 could be inflated from the same source as that used to inflate a proximal seal 50, or they may be inflated by a separate source, either after introduction into the bowel, during introduction, or before introduction.

Figure 15A:
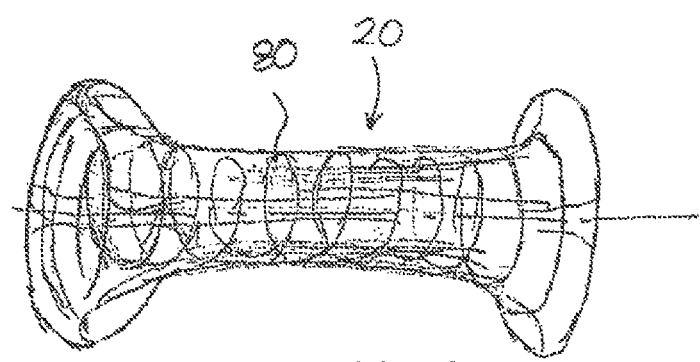
FIG. 15A is a schematic perspective view of a fourteenth embodiment of stoma adapter.
Figure 15B:
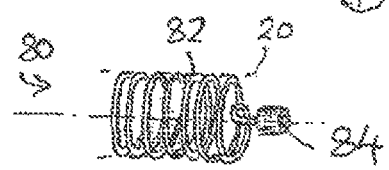
FIG. 15B is a schematic perspective view of a fifteenth embodiment of stoma adapter.
Figure 15C:
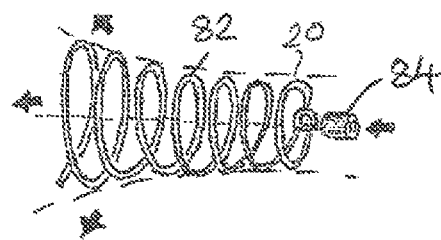
FIG. 15C is a schematic perspective view of a fifteenth embodiment of stoma adapter.

Referring to FIGS. 15*a*, 15B and 15C, in another embodiment, a helical spring 80 is used to impart an appropriate level of resistance to axial force while allowing a high level of radial compliance. In one form (FIG. 15A), the spring 80 is mechanical in nature; that is, formed from an elastic material such as a metal or polymer. In another form (FIGS. 15B and 15C), the spring 80 is formed from a flexible tube 82 with a helical shape. The flexible tube 82 is attached to or incorporated into the stoma adapter 20 in the same manner as the tubes 76 of FIGS. 14A and 14B. The flexible tube 82 would have no intrinsic strength when not inflated (FIG. 15B). When inflated (FIG. 15C) to a desired inflation pressure through inflation port 84, the flexible tube 82 exhibits the desired level of axial stiffness yet maintaining radial compliance.

In another embodiment (not shown), longitudinal buttress or reinforcing elements could be made of a material with different physical properties than the main tube of the stoma adapter 20. Such reinforcing elements could, for example, be incorporated into the stoma adapter 20 by co-extrusion.

In another embodiment (not shown) the axial stiffness of the stoma adapter 20 could be enhanced by selectively coating the stoma adapter 20 in specific areas with materials that modify the properties of the tube 76, 82 by either imparting their own stiffness to enhance the stiffness of the entire structure or by locally modifying the properties of the stoma adapter 20 material itself.

Another aspect of the stoma adapter 20 is insertion in the stoma 10 and/bowel. The following embodiments illustrate various insertion principles. Although these embodiments illustrate insertion features separately, the insertion arrangements may be combined, and any of the insertion arrangements may be used with any of the preceding embodiments.

Figure 16A:
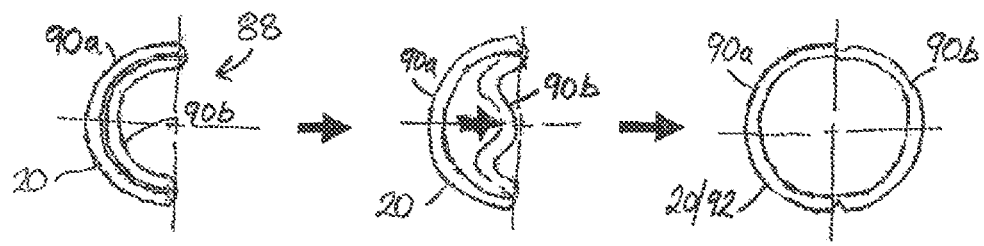
FIG. 16A is a progression of end-section views showing deployment of a sixteenth embodiment of stoma adapter.
Figure 16B:
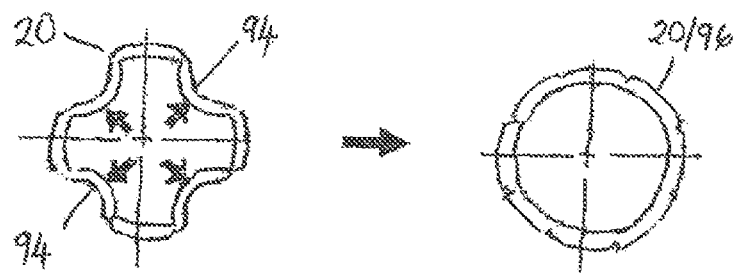
FIG. 16B is a progression of end-section views showing deployment of a seventeenth embodiment of stoma adapter.

If the stoma adapter 20 is rigid, or at least semi-rigid, introduction of the proximal end 22 into the bowel is likely to require a degree of radial stretching or compliance of the bowel at one or more locations along the length of the stoma adapter 20. FIGS. 16A and 16B illustrate an idea of collapsing cross-section configurations that may be employed to minimize (or at least reduce) the amount of compliance or stretching of the bowel during introduction of the stoma adapter 20. By creating a bistable cross section 88, it is possible to more easily introduce the proximal end 22 of the stoma adapter 20 in its collapsed configuration, and then expand it to its final configuration after insertion. In one embodiment (FIG. 16A), the collapsed configuration of the stoma adapter 20 is, in cross section, two adjacent semi-circular shapes 90*a* and 90*b*. Upon insertion, the stoma adapter 20 is expanded by driving out the inner semi-circular shape 90*b* until the stoma adapter expands, in cross section, into a complete loop 92 (e.g., circle) after introduction. In another embodiment (FIG. 16B), the collapsed configuration of the stoma adapter 20 has a fluted cross section, with flute segments or channels 94 that give the stoma adapter 20 a reduced overall diameter. After insertion, the fluted cross-section is expanded to its final circular shape 96.

Expansion of the collapsed configuration after introduction of the proximal end 22 into the stoma 10 could be accomplished by means of a mandrel (not shown) which could be inserted into the stoma adapter 20 and then expanded to initiate the shape change. Such a mandrel could be mechanical in nature, but a desirable embodiment may be an inflatable cylinder which could be inflated to the appropriate diameter to expand the stoma adapter 20 to its final shape. In another embodiment, elements made of a shape-memory material expand after introduction and exposure to body temperature, causing the stoma adapter 20 to expand to its final shape.

Figure 17:
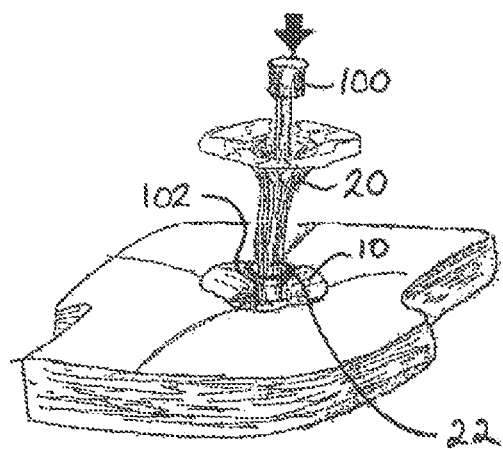
FIG. 17 is a schematic perspective view showing use of an applicator for aiding insertion of a stoma adapter into the stoma.

Referring to FIG. 17, if the stoma adapter 20 is non-rigid or flexible, at least in the axial direction (e.g., as in the embodiments of FIGS. 14A, 14B, 15B and 15C when not inflated), it may be desirable to employ an insertion device 100 to aid insertion of the proximal end 22 into the stoma 10. To improve ease of insertion, the cross section of the stoma adapter 20 is preferably reduced or minimized, especially at the proximal end 22. This is accomplished by selectively folding and pleating the flexible material of the stoma adapter 20 into a cross section size and shape that is more easily introduced into the bowel. Once introduced, the material of the stoma adapter 20 may be unfolded and deployed by mechanical means or pneumatic means, for example using the same component as the insertion device 100, or using a different component (not shown). If required, the insertion device 100 used to assist in the introduction of the stoma adapter 20 into the bowel could be removed.

The stoma adapter 20 may be held captive in its folded state by a constricting element 102 that can be removed or released after introduction into the stoma 10. The constricting element 102 may be arranged at the proximal end 22 of the stoma adapter 20.

Figure 18:
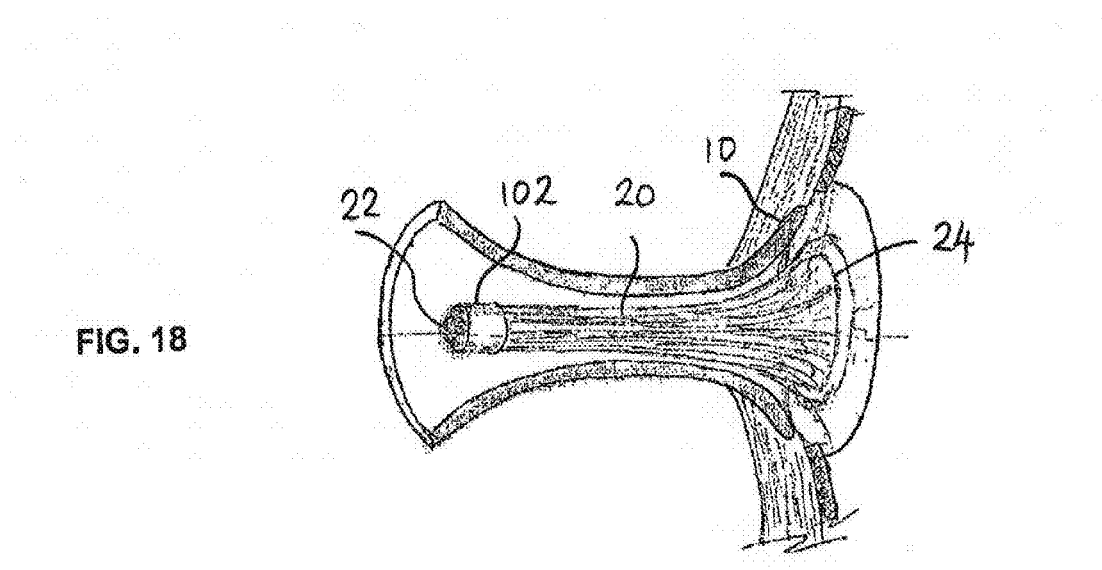
FIG. 18 is a schematic side view of an eighteenth embodiment of stoma adapter.

Referring to FIG. 18, one form of such a constricting element 102 may be made of biocompatible material that dissolves or is absorbed shortly after introduction of the stoma adapter 20 into the stoma 10. For example, the constricting element 102 may dissolve upon contact with stomal fluid. In the illustrated form, the constricting element 102 is a tightly-formed band or collar made of the biocompatible material.

Figure 19A:
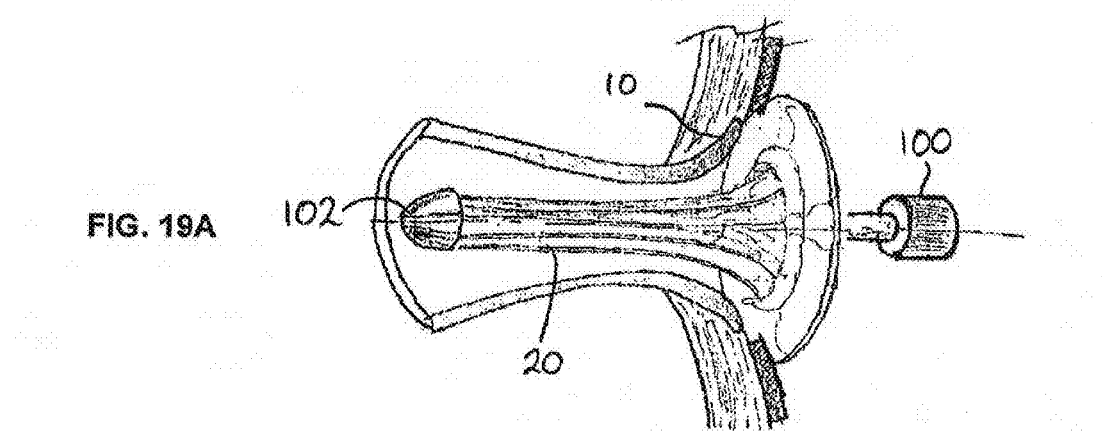
FIG. 19A is a schematic side view of a nineteenth embodiment of stoma adapter.
Figure 19B:
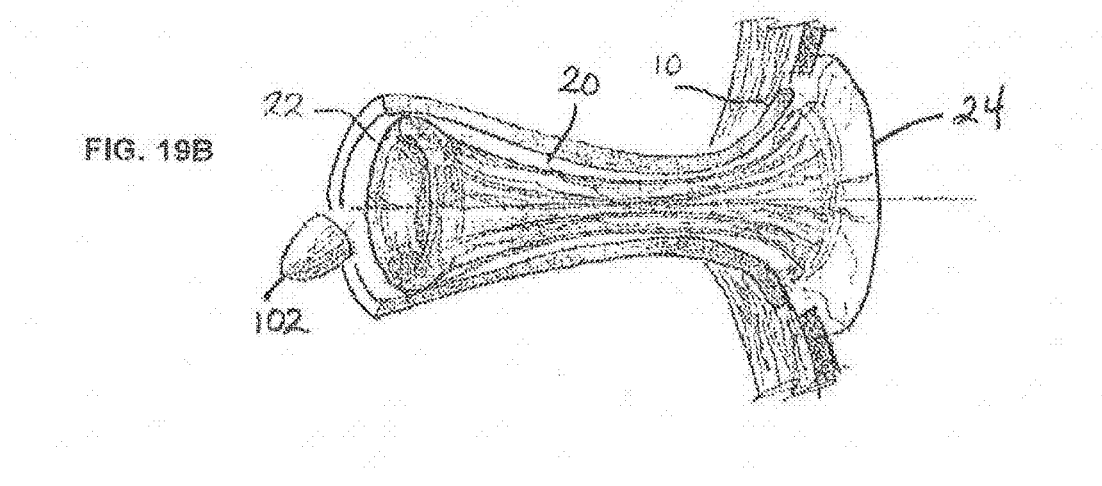
FIG. 19B is a schematic side view of a nineteenth embodiment of stoma adapter.

Referring to FIGS. 19A and 19B, in another embodiment the constricting element 102 is in the form of a conical tip for holding the stoma adapter 20 in its folded state. The cone could be formed from a dissolvable material, as described above. Additionally or alternatively, an insertion device 100 may be employed to introduce stoma adapter 20 and dislodge the constricting element (conical tip) 102. For example, the constricting element (conical tip) 102 may be dislodged when the stoma adapter 20 reaches its fully inserted position, and the constricting element (conical tip) 102 then bears the full insertion force applied through the insertion device 100. The insertion device 100 would then be withdrawn through the distal end 24 of the stoma adapter 20.

Materials for these constricting elements 102 include, but are not limited to, biocompatible materials of natural or synthetic origin such as polysaccharides, cellulosics such as hydroxypropylmethyl cellulose, hydroxyethyl cellulose, hydroxypropyl cellulose, carboxymethyl cellulose, chitosan and its derivatives, gelatin, alginates, sodium alginate, xanthan gum, tragacantha, guar gum, acacia gum, arabic gum, polyacrylic acid and its copolymers, polypeptides, sulfonated polymers, polyacrylamide and its copolymers, polyvinyl pyrrolidone, polyvinyl ether, polyvinyl alcohol, polyethylene, glycol, x, methylmethacrylate copolymers, and carboxyvinyl polymers and copolymers.

Figure 20A:
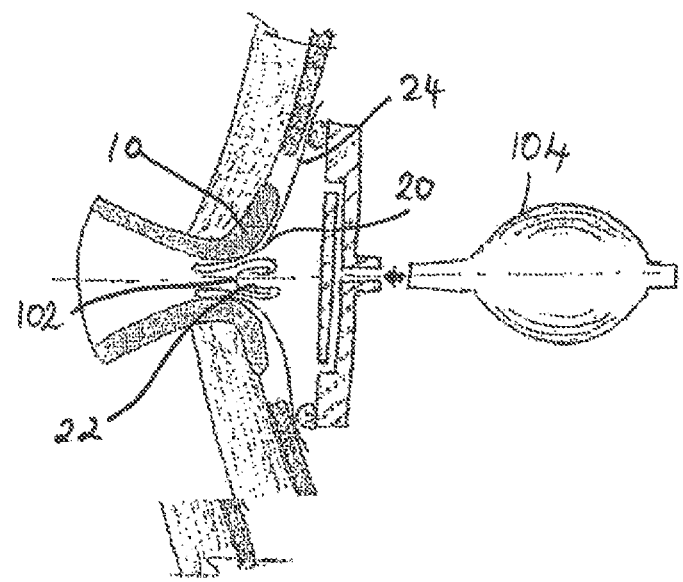
FIG. 20A is a schematic sectional view showing insertion and deployment of a twentieth embodiment of stoma adapter.
Figure 20B:
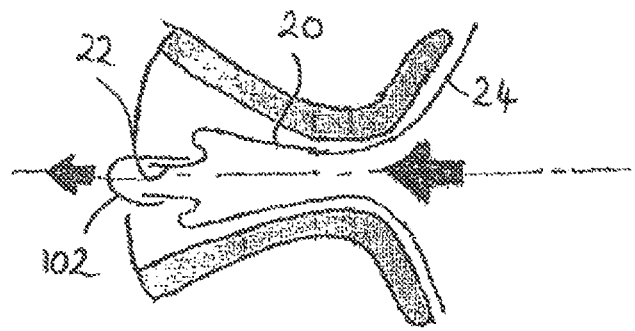
FIG. 20B is a schematic sectional view showing insertion and deployment of a twentieth embodiment of stoma adapter.
Figure 20C:
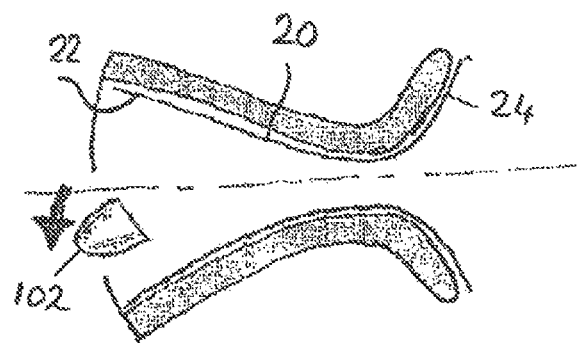
FIG. 20C is a schematic sectional view showing insertion and deployment of a twentieth embodiment of stoma adapter.

Referring to FIGS. 20A, 20B and 20C, in another embodiment, the stoma adapter 20 could be partially inverted into a folded shape (FIG. 20A) and its proximal end 22 temporarily closed with a constricting element or tip 102. In use, the stoma adapter 20 in its inverted condition is partially introduced into the stoma 10 (FIG. 20A), and then a moderate amount of air or saline is applied from a pressurization source 104 to pressurize the distal end of the stoma adapter. As illustrated in FIGS. 20B and 20C, the pressure causes the stoma adapter 20 to unfold, and thus introduce the proximal end 22 into the bowel as the stoma adapter 20 unfolds.

It will be appreciated that the stoma adapter of the present invention can provide effluent guidance and skin protection for all types of stoma, but is especially suitable for recessed or flush stomas, which are difficult to manage. The stoma adapter may be independent of the ostomy appliance with which it is used, or the stoma adapter may be attachable to the ostomy appliance or an integral part of the ostomy appliance. The stoma adapter may take many different rigid or non-rigid forms, depending on the desired characteristics.

Many modifications may be made to the preferred embodiments used without departing from the claim coverage of the invention.

The invention claimed is:

1. A stoma adapter comprising:
    a substantially unobstructed tubular passageway for expulsion of effluent with a proximal end for attachment in or around a stoma and a distal end for discharge of waste, the distal end comprising a flange,
    a flexible tubular wall surrounding said entire tubular passageway, said flexible tubular wall having at least one axial reinforcement element for reinforcing said flexible tubular wall in an axial direction to provide axial stiffness along the entire tubular passageway and permit flexing of the flexible tubular wall in a radial direction, and
    a one-way valve, wherein the one-way valve prevents re-entry of discharged waste into the distal end of the tubular passageway, wherein the one-way valve is openable from a closed position by pressure of the effluent when a bowel forces the expulsion of the effluent, wherein the one-way valve is disposed at the distal end.

2. The stoma adapter of claim 1 wherein at least one reinforcement element is inflatable.

3. The stoma adapter of claim 1 wherein at least one reinforcement element is a helical compression spring.

4. The stoma adapter of claim 3 wherein the helical compression spring is formed from metal.

5. The stoma adapter of claim 3 wherein the helical compression spring is formed from polymer.

6. The stoma adapter of claim 3 wherein the helical compression spring is formed from a flexible and inflatable tube with a helical shape.

7. The stoma adapter of claim 1 wherein the flange releasably or permanently engages the stoma adapter to a body fitment attached to an ostomy pouch.

8. The stoma adapter of claim 7 wherein the body fitment is secured to a subject's periostomal skin by an adhesive attachment.

9. The stoma adapter of claim 8 wherein the body fitment is secured to a subject's periostomal skin.

10. The stoma adapter of claim 7 wherein the flange is attached to the body fitment by a mechanical fastener.

11. The stoma adapter of claim 7 wherein the flange is attached to the body fitment by an adhesive attachment.

12. The stoma adapter of claim 7 wherein the flange is trapped between the periostomal skin and the body fitment to hold the stoma adapter in position.

13. The stoma adapter of claim 7 wherein the stoma adapter provides direct transport of effluent from the bowel into an ostomy pouch attached to the body fitment.

14. The stoma adapter of claim 1, wherein the axial reinforcement element spans the entire length of the stoma adapter.

* * * * *